US012766317B2

(12) United States Patent
Cho

(10) Patent No.: US 12,766,317 B2
(45) Date of Patent: Oct. 20, 2026

(54) ELECTRICAL STIMULATION SYSTEM FOR IMPROVING VERTEBRAL SYNOSTOSIS

(71) Applicant: KYUNGPOOK NATIONAL UNIVERSITY INDUSTRY-ACADEMIC COOPERATION FOUNDATION, Daegu (KR)

(72) Inventor: Daechul Cho, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 19/126,247

(22) PCT Filed: Oct. 23, 2023

(86) PCT No.: PCT/KR2023/016449
§ 371 (c)(1),
(2) Date: Apr. 30, 2025

(87) PCT Pub. No.: WO2024/096413
PCT Pub. Date: May 10, 2024

(65) Prior Publication Data

US 2026/0166314 A1 Jun. 18, 2026

(30) Foreign Application Priority Data

Nov. 1, 2022 (KR) ........................ 10-2022-0143804

(51) Int. Cl.
*A61N 1/32* (2006.01)
*A61F 2/44* (2006.01)
(Continued)

(52) U.S. Cl.
CPC ............ *A61N 1/326* (2013.01); *A61F 2/4455* (2013.01); *A61N 1/3787* (2013.01); *A61F 2002/2821* (2013.01)

(58) Field of Classification Search
CPC ....... A61F 2002/2821; A61F 2/44–447; A61N 1/326; A61N 1/3787
See application file for complete search history.

(56) References Cited

U.S. PATENT DOCUMENTS 6,034,295 A * 3/2000 Rehberg ................. A61B 17/72 607/51
6,319,255 B1 * 11/2001 Grundei ................. A61B 17/70 606/76

(Continued)

FOREIGN PATENT DOCUMENTS

CN 115568987 A * 1/2023 ........... A61F 2/4455
JP 2018-521735 A 8/2018

(Continued)

*Primary Examiner* — Jacqueline T Johanas
(74) *Attorney, Agent, or Firm* — Bridgeway IP Law Group, PLLC; Sang Ho Lee; Hyun Woo Shin

(57) ABSTRACT

An electrical stimulation system for improving vertebral synostosis including a spinal cage formed with a porous structure in which a front side and a rear side are occluded, and inserted between a user's vertebrae to deliver electrical stimulation to the user, and a power supply device configured to transmit wireless power for generating electrical stimulation to the spinal cage, and enabling the user to wear the power supply device. Thus, the electrical stimulation system can enhance a user's spinal bone fusion.

8 Claims, 4 Drawing Sheets

(51) Int. Cl.
*A61N 1/378* (2006.01)
*A61F 2/28* (2006.01)

(56) References Cited

U.S. PATENT DOCUMENTS

| | | | | |
|---|---|---|---|---|
| 10,123,882 | B2 * | 11/2018 | Stevenson | A61F 2/30767 |
| 10,292,831 | B2 | 5/2019 | Zellmer et al. | |
| 10,617,880 | B2 | 4/2020 | Zellmer et al. | |
| 12,582,818 | B2 * | 3/2026 | Zellmer | A61N 1/326 |
| 2004/0024400 | A1 * | 2/2004 | Michelson | A61F 2/4455 606/41 |
| 2016/0270927 | A1 * | 9/2016 | Zellmer | A61B 5/4504 |
| 2017/0007420 | A1 | 1/2017 | Stevenson et al. | |
| 2017/0157407 | A1 * | 6/2017 | Zellmer | A61N 1/3787 |
| 2020/0069247 | A1 | 3/2020 | Hunter | |
| 2020/0352723 | A1 * | 11/2020 | Jimenez | A61F 2/4611 |
| 2026/0166314 | A1 * | 6/2026 | Cho | A61F 2/447 |

FOREIGN PATENT DOCUMENTS

| | | | | |
|---|---|---|---|---|
| KR | 10-2012-0028928 | A | 3/2012 | |
| KR | 10-2016-0128236 | A | 11/2016 | |
| KR | 10-2151554 | B1 | 9/2020 | |
| KR | 10-2021-0087342 | A | 7/2021 | |
| KR | 10-2022-0076136 | A | 6/2022 | |
| KR | 20240061915 | A * | 5/2024 | H02J 50/12 |

* cited by examiner

ELECTRICAL STIMULATION SYSTEM FOR IMPROVING VERTEBRAL SYNOSTOSIS

TECHNICAL FIELD

The present invention relates to an electrical stimulation system for improving the vertebral synostosis, and more particularly, to an electrical stimulation system for improving the vertebral synostosis by providing electrical stimulation through a spinal cage inserted between vertebrae.

BACKGROUND ART

The vertebral body is composed of 32 to 35 vertebrae, which form the torso, and intervertebral disks between the vertebrae and constitutes the central axis of the human body that connects the skull of the top and the pelvis of the bottom.

The vertebrae consist of seven cervical vertebrae, twelve thoracic vertebrae, five lumbar vertebrae, five sacral vertebrae, and three to five coccygeal vertebrae from top to bottom. In adults, the five sacral vertebrae are fused into one sacrum, and the three to five coccygeal vertebrae are fused into one coccyx.

In most people, disease or accidents may cause the disk to rupture or weaken, resulting in pain due to compression of the spinal nerves. In such cases, spinal fusion surgery is performed, which removes the damaged disk and inserts a cage that is an artificial correction device between adjacent vertebrae to restore and maintain the intervertebral spacing.

In such spinal fusion surgery, it is important to increase bone integration between the implanted cage and the vertebrae. To this end, the cage with an internal hollow space to allow bone growth are being designed, and attempts to fill the hollow space with autograft, allograft, or synthetic bone have been continuously made to promote bone growth.

In this regard, in the medical field, a spinal cage is being designed to be porous so that, when implanted into the body, bone ingrowth occurs in macropores existing within the cage, thereby shortening the time required for fixation of the spinal cage and increasing fixation strength.

As such, the cage inserted between the vertebrae has an appropriate thickness and an anatomic type to restore the original height of the intervertebral disk, is formed with a porous structure to facilitate the bone growth by inserting a patient's autologous bone, and includes a mounting structure for attaching an insertion tool.

However, simply forming the spinal cage with the porous structure facilitates integration with surrounding bone tissues, but cannot absorb the axial compression force of the vertebrae after being inserted between the vertebrae, resulting in a problem of reducing strength for supporting the vertebrae.

Therefore, there is a need to develop a technique to enhance the spinal bone fusion when the cage is inserted between the vertebrae.

RELATED ART LITERATURE

Patent Literature

Patent Literature 1: Korean Patent Publication No. 10-2016-0128236

DISCLOSURE

Technical Problem

Accordingly, the present invention has been made in view of the above-mentioned problems occurring in the related art, and it is an object of the present invention to provide an electrical stimulation system for improving vertebral synostosis, which provides electrical stimulation by inserting a spinal cage combined with a receiving coil capable of generating electrical stimulation between the vertebrae of a patient.

Technical Solution

To accomplish the above-mentioned objects, according to the present invention, there is provided an electrical stimulation system for improving vertebral synostosis including a spinal cage having a porous structure with a front side and a rear side are occluded, and inserted between a user's vertebrae to deliver electrical stimulation to the user; and a power supply device configured to transmit wireless power for generating electrical stimulation to the spinal cage, and enabling the user to wear the power supply device.

Here, the power supply device includes: a battery; a transmission circuit configured to wirelessly transmit power stored in the battery to the spinal cage; and a control unit configured to induce magnetic resonance in the transmission circuit using the power stored in the battery.

Moreover, the control unit adjusts a voltage level of magnetic resonance generated in the transmission circuit based on control information input from the exterior.

Furthermore, the spinal cage comprises a cage body formed to surround a hollow portion which is a bone graft filling space, wherein the cage body includes: a front end portion tapered toward a front end; a rear end portion formed flat at a position facing the front end portion; the hollow portion formed between the front end portion and the rear end portion as the bone graft filling space; and a side portion forming the side surface of the hollow portion, and partially opened to have a porous structure.

Here, the side portion includes: a plurality of contact surfaces forming upper and lower surfaces of the side portion and being in contact with the vertebrae; a plurality of protrusions formed on the contact surfaces at predetermined intervals in a longitudinal direction; and a plurality of plate springs positioned between the plurality of contact surfaces and configured to be deformed in response to axial pressure applied in a vertical direction.

Additionally, the side portion further comprises a plurality of receiving coils positioned adjacent to the contact surfaces to generate electrical stimulation on the contact surfaces.

In addition, the plurality of receiving coils are positioned on the outer surface of the side portion corresponding to the contact surfaces, and comprise a metal part and a wire surrounding the metal part.

Meanwhile, the electrical stimulation system further includes a user terminal configured to output a stimulation control interface screen to the user for controlling the electrical stimulation, generate control information based on a stimulation control item selected by the user through the stimulation control interface screen, and transmit the control information to the power supply device.

Advantageous Effect

The electrical stimulation system for improving vertebral synostosis according to an embodiment of the present invention can improve bone fusion between the user's vertebrae by inserting the spinal cage between the user's vertebrae and generating electrical stimulation using the spinal cage.

MODE FOR INVENTION

Figure 1:
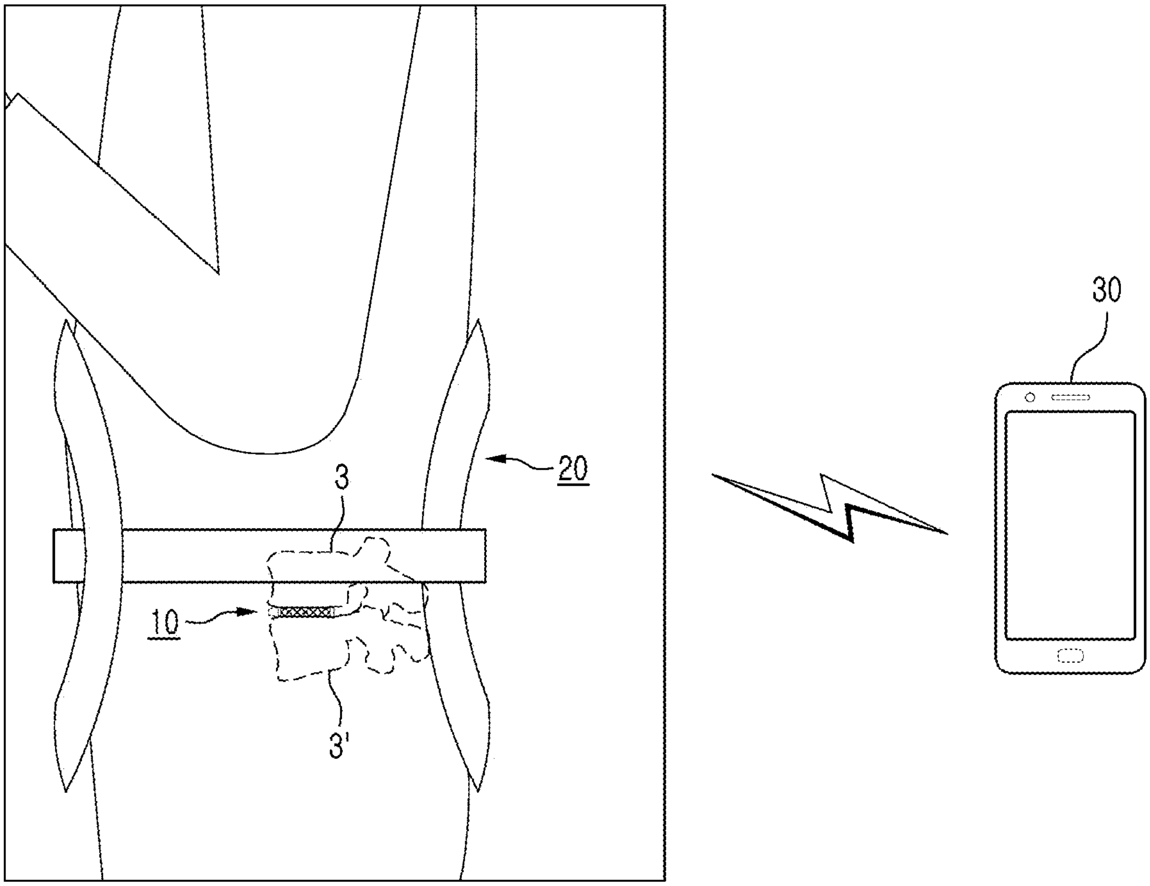
FIG. 1 is an exemplary view of an electrical stimulation system for improving vertebral synostosis according to an embodiment of the present invention.

Specific embodiments of the present invention are described in detail below with reference to the accompanying drawings. The embodiments are described in detail in order for those skilled in the art to readily implement the present invention. It is to be understood that the various embodiments of the present invention are different from each other, but do not need to be exclusive. For example, a specific shape, structure and characteristic described in this specification in connection with an embodiment may be implemented as another embodiment without departing from the spirit and scope of the present invention. It is also to be understood that the position or arrangement of an individual element within each disclosed embodiment may be changed without departing from the spirit and scope of the present invention. Accordingly, the detailed description hereinafter is not intended to have a limited meaning, and the range of right of the present invention is restricted by only the attached claims along with the entire range equivalent to things claimed by the claims, if it is appropriately described. Similar reference numerals in the drawings denote the same or similar functions from several aspects.

Terms used in the specification are provided for description of the exemplary embodiments, and the present invention is not limited thereto. In the specification, singulars in sentences include plural unless otherwise noted. It will be understood in the specification that the terms "comprises" and "comprising", when used herein, specify the presence of constituent elements, but do not preclude the presence or addition of other constituent elements. Throughout the specification, the same reference numerals refer to the same components, and "and/or" includes each and all combinations of the mentioned components. Although terms such as "first" and "second" may be used to describe various components, the components are not limited by such terms. The terms are used only to distinguish one component from another. Therefore, a first component referred to below may also be a second component within the spirit of the present invention.

Unless otherwise defined, all terms used in this specification have the same meanings commonly understood by those skilled in the art to which the present invention belongs. Also, terms defined in commonly used dictionaries are not to be interpreted ideally or excessively unless explicitly defined otherwise.

Hereinafter, preferred embodiments of the present invention will be described in more detail with reference to the drawings.

Figure 2:
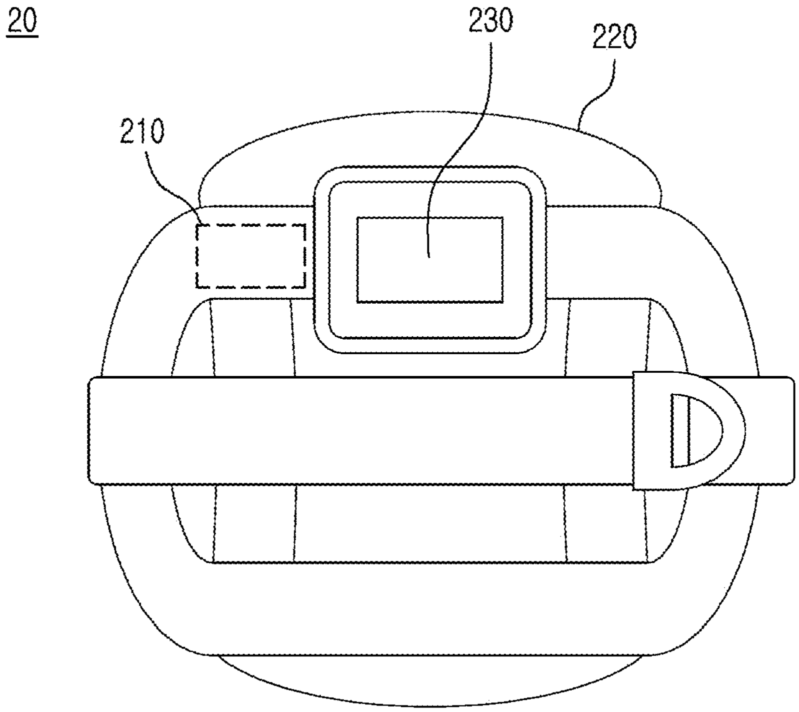
FIG. 2 is an exemplary view of a power supply device of FIG. 1.
Figure 3:
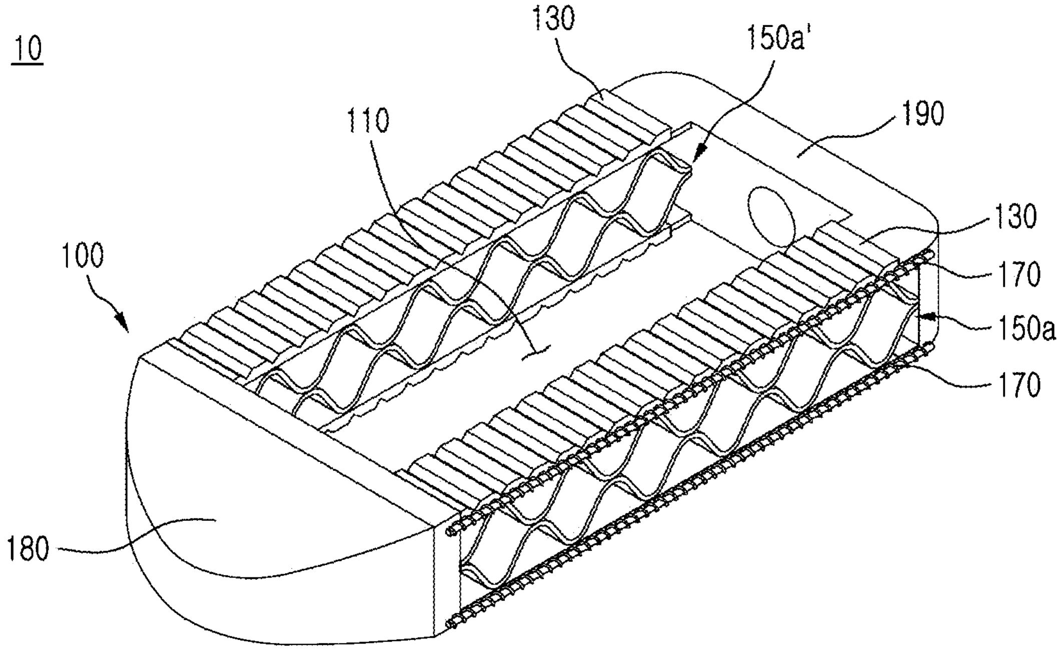
FIG. 3 is a perspective view of a spinal cage of FIG. 1.
Figure 4:
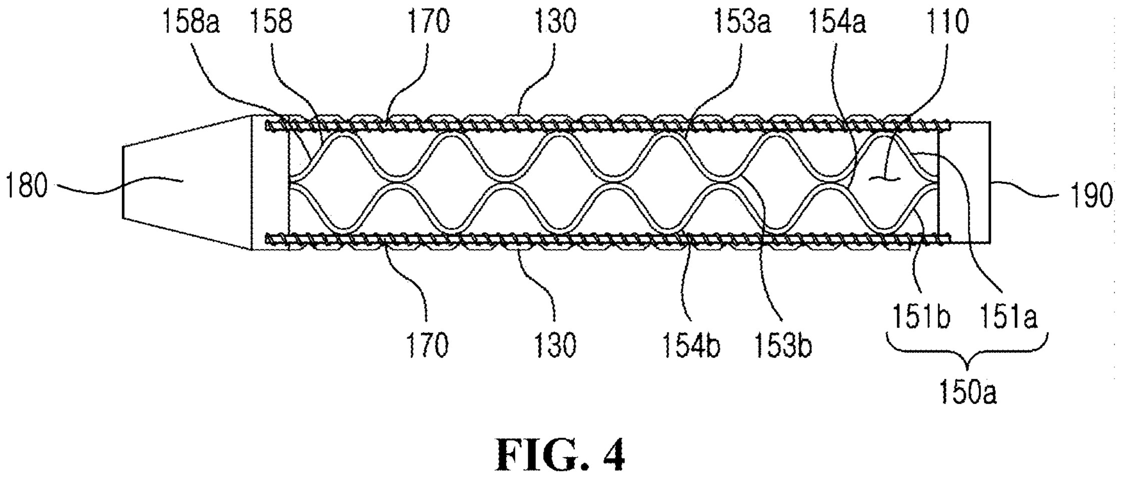
FIG. 4 is a side cross-sectional view of the spinal cage of FIG. 1.
Figure 5:
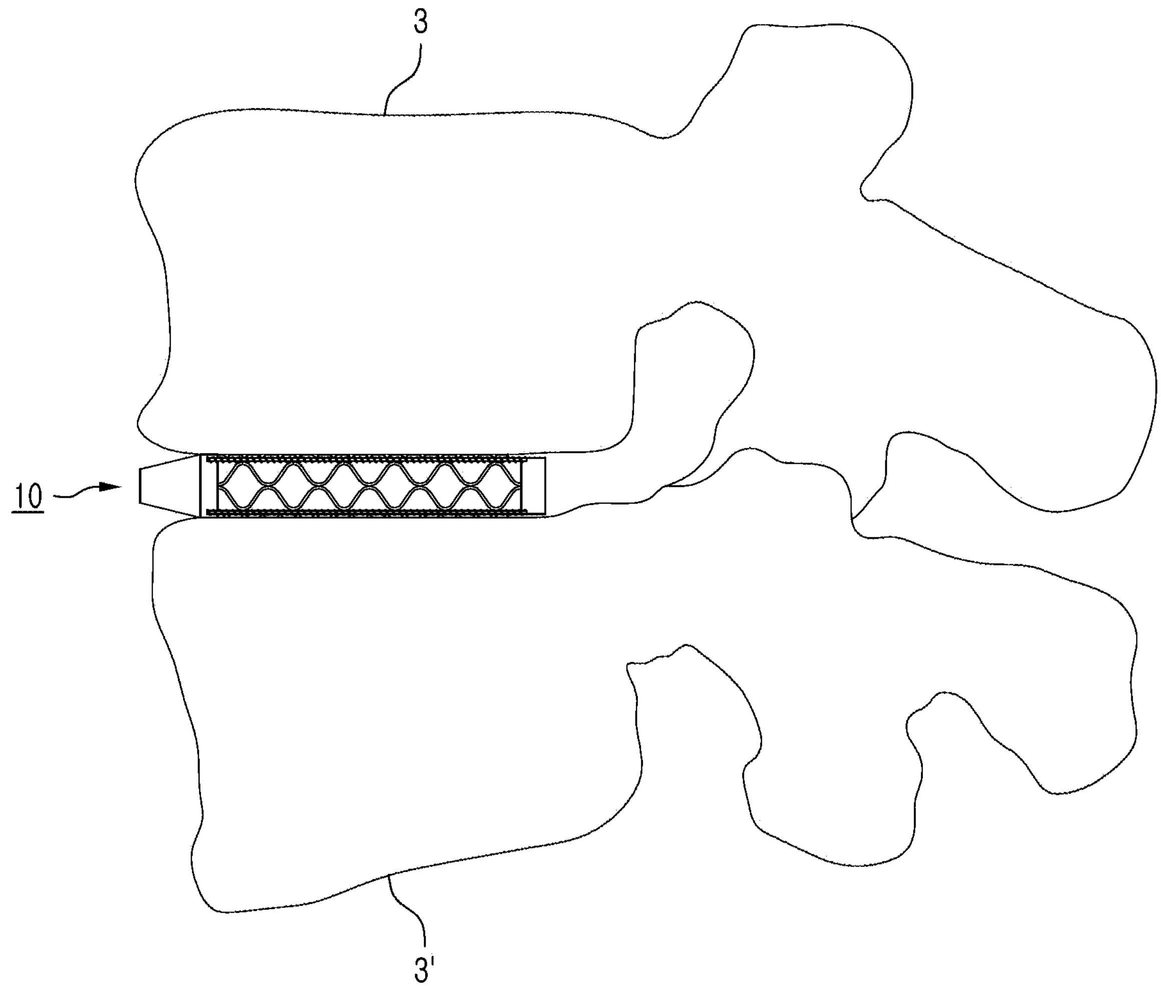
FIG. 5 is an exemplary view illustrating the spinal cage of FIG. 1 inserted between a user's vertebrae.

FIG. 1 is an exemplary view of an electrical stimulation system for improving vertebral synostosis according to an embodiment of the present invention, FIG. 2 is an exemplary view of a power supply device of FIG. 1, FIG. 3 is a perspective view of a spinal cage of FIG. 1, FIG. 4 is a side cross-sectional view of the spinal cage of FIG. 1, and FIG. 5 is an exemplary view illustrating the spinal cage of FIG. 1 inserted between a user's vertebrae.

According to an embodiment of the present invention, an electrical stimulation system for improving vertebral synostosis (hereinafter, referred to as 'system') 1 inserts a spinal cage 10 with a receiving coil 170 between vertebrae 3 and 3' of a user, and generates electrical stimulation through a power supply device 20.

Referring to FIG. 1, the system 1 includes the power supply device 20 formed in the shape of an orthosis and the spinal cage 10 formed with a porous structure.

Moreover, the system 1 further includes a user terminal 30 for the user to control the electrical stimulation.

Here, the user terminal 30 outputs a stimulation control interface screen for allowing the user in whom the spinal cage 10 is inserted to control the electrical stimulation, generates control information based on a stimulation control item selected by the user via the stimulation control interface screen, and transmits the control information to the power supply device 20.

The user terminal 30 can communicate with the power supply device 20 via a network. The network refers to a connection structure capable of exchanging information between nodes such as terminals and servers, and includes Internet, wireless local area network (Wireless LAN), wide area network (WAN), personal area network (PAN), 3G, 5G, long term evolution (LTE), wireless fidelity (WiFi), world interoperability for microwave access (WiMAX), and wireless gigabit (WiGig).

Furthermore, the user terminal 30 may be in the form of a server or an engine that can be mobile or fixed, and may be referred to by other terms such as device, apparatus, terminal, user equipment (UE), mobile station (MS), wireless device, or handheld device.

The power supply device 20 transmits wireless power to the spinal cage 10 to generate electrical stimulation.

The power supply device 20 may be provided in various forms such as a belt type or a pocket type so that the power supply device 20 can be worn by the user.

More specifically, the power supply device 20 may be provided in various forms depending on the position of the user's vertebrae in which the spinal cage 10 is inserted.

Here, if the vertebrae in which the spinal cage 10 is inserted are the cervical vertebrae (1st to 3rd cervical vertebrae) adjacent to the user's skull, the power supply device 20 may be formed in the shape of a cervical brace (CervicalStim Device).

Additionally, if the vertebrae in which the spinal cage 10 is inserted are the thoracic and lumbar vertebrae adjacent to the user's thoracic region, the power supply device 20 may be formed in the shape of a lumbar brace (SpinalStim Device).

Referring to FIG. 2, the power supply device 20 may include a battery 210, a transmission circuit 220, a control unit 230, and a communication unit for network communication with the user terminal 30. Here, the communication unit is a communication sensor or a communication module for receiving control information from the user terminal 30 and may communicate through a network via known communication methods. Therefore, a detailed description thereof will be omitted herein.

The battery 210 may be charged by receiving operation power from an external source.

Here, the battery 210 may be integrally provided in the power supply device 20, or may be configured to be replaceable in the power supply device 20.

Although not illustrated in the drawings, the battery 210 may be charged by receiving commercial power from an external source through a charging port provided on one side of the power supply device 20.

The transmission circuit 220 may wirelessly transmit the power stored in the battery 210 to the spinal cage 10.

More specifically, the transmission circuit 220 is a circuit configured to generate and wirelessly transmit a resonance signal of a predetermined resonance frequency, and may include a transmission coil having the same magnetic resonance frequency as a receiving coil 170 formed in the spinal cage 10. In this case, the transmission coil may be a coil in which a source coil and a transmission resonance coil are combined.

Here, the transmission circuit 220 may form a path between the transmission coil and the receiving coil 170 formed in the spinal cage to generate a resonance phenomenon, thereby increasing wireless power transfer efficiency.

Moreover, the transmission circuit 220 may include a power amplifier that amplifies the level of power supplied from the battery 210, a matching circuit that generates a resonant signal by matching the frequency of the amplified signal for power transmission via magnetic resonance method, and a transmission controller that controls the operation of the power amplifier and the matching circuit.

In addition, the transmission circuit 220 may further include a resonator that performs wireless power transmission via magnetic resonance method. Here, the resonator may be formed as a loop antenna or a helical antenna having a circular or rectangular wire.

The control unit 230 may induce magnetic resonance of the transmission circuit 220 using the power stored in the battery 210. Here, the control unit 230 may be provided as a main control module (modulation) that controls the operation of each component included in the power supply device 20.

The control unit 230 may adjust the voltage level of magnetic resonance generated in the transmission circuit according to control information input from the outside.

More specifically, when control information is received from an external source, i.e., the user terminal 30, the control unit 230 may identify a resonance frequency value corresponding to the control information in a separately provided memory and adjust the voltage level of the resonance signal at the identified resonance frequency.

Accordingly, the power supply device 20 may wirelessly transmit power to the spinal cage 10 according to the user's adjustment.

The spinal cage 10 is inserted and installed between the user's vertebrae 3 and 3' and generates electrical stimulation according to the power received from the power supply device 20 via the receiving coil 170.

Referring to FIGS. 3 and 4, the spinal cage 10 includes a cage body 100 formed to surround a hollow portion which is a bone graft filling space 110.

The cage body 100 has the hollow portion formed at the center thereof and has an overall rectangular parallelepiped shape elongated in the longitudinal direction.

More specifically, the cage body 100 may include a front end portion 180 having a tapered shape toward the front end, a rear end portion 190 formed flat and facing the front end portion 180, the hollow portion as the bone graft filling space 110 formed between the front end portion 180 and the rear end portion 190, and side portions forming the side surfaces of the hollow portion and partially opened to have a porous structure.

Here, the side portions include a plurality of contact surfaces that form upper and lower surfaces and contact the user's vertebrae 3 and 3', a plurality of protrusions 130 formed on the contact surfaces, and a plurality of plate springs 150.

More specifically, the plurality of protrusions 130 of the cage body 100 may be protrudingly formed on the surfaces of the side portions, which contact the vertebrae 3 and 3', at predetermined intervals in the longitudinal direction.

Here, by having the plurality of protrusions 130, the cage body 100 may be closely fixed to the adjacent vertebrae 3 and 3' when inserted therebetween.

As illustrated in FIGS. 3 and 4, the plurality of protrusions 130 may be formed in a hexahedral shape with rough upper and lower surfaces to be closely fixed to the vertebrae 3 and 3', but are not limited thereto as they may also be formed in a wedge shape, and may be formed in various shapes that can be easily fixed to the vertebrae 3 and 3'.

In addition, the cage body 100 may have a hole penetrated through the center of the rear end portion 190 to allow a surgical tool or the like to be coupled for inserting the spinal cage 10 between the vertebrae 3 and 3'.

Furthermore, the cage body 100 may include a plurality of plate springs **150*a* and 150*a*'** located between the plurality of contact surfaces forming the side portions and deformed according to axial pressure applied in the vertical direction.

Referring to FIG. 5, the plurality of plate springs **150*a* and 150*a*'** may be installed on the upper and lower sides of the side portion to face each other.

Here, the plate springs **150*a* and 150*a*' are springs that extend in a plate shape and have elasticity, and may be provided as a pair of an upper plate spring 151*a* and a lower plate spring 151*b*** respectively provided on the upper and lower sides.

The upper plate spring **151*a* and the lower plate spring 151*b*** may substantially extend as long as the longitudinal direction of the side portion.

In this regard, the widthwise length of the upper plate spring **151*a* and the lower plate spring 151*b* may be formed to correspond to the horizontal width of the edge formed on the cage body 100**.

Furthermore, the upper plate spring **151*a* and the lower plate spring 151*b* may be formed in a wave shape in which a plurality of crest portions 153*a* and 154*a* and trough portions 153*b* and 154*b*** are continuously formed.

Here, the crest portions **153*a* of the upper plate spring 151*a* and the trough portions 154*b* of the lower plate spring 151*b* may be arranged to respectively contact the upper surface and the lower surface of both edges of the bone graft filling space 110**.

Additionally, the trough portions **153*b* of the upper plate spring 151*a* and the crest portions 154*a* of the lower plate spring 151*b* may be arranged to contact each other such that the upper and lower plate springs 151*a* and 151*b*** are symmetrical.

More specifically, the centers of the outer surfaces of the crest portions **153*a* of the upper plate spring 151*a* may be arranged to contact the lower surfaces of both edges of a frame shape formed on the upper portion of the bone graft filling space 110**.

Moreover, the centers of the outer surfaces of the trough portions **154*b* of the lower plate spring 151*b* may be arranged to contact the upper surfaces of both edges of a frame shape formed on the lower portion of the bone graft filling space 110**.

Furthermore, the centers of the outer surfaces of the trough portions **153*b* of the upper plate spring 151*a* and the centers of the outer surfaces of the crest portions 154***a* of the lower plate spring 151*b* may be arranged to contact each other.

In this regard, the thickness of the crest portions 153*a* and 154*a* and the trough portions 153*b* and 154*b* of the upper and lower plate springs 151*a* and 151*b* may be formed differently from the thickness of the connection portions 158 connecting the crest portions 153*a* and 154*a* and the trough portions 153*b* and 154*b*.

More specifically, the crest portions 153*a* and 154*a* and the trough portions 153*b* and 154*b* of the upper and lower plate springs 151*a* and 151*b* may be formed with the same thickness, and the connection portions 158 connecting the crest portions 153*a* and 154*a* and the trough portions 153*b* and 154*b* may be formed such that their thickness gradually decreases in the direction toward a center portion 158*a*.

Meanwhile, the spinal cage 10 may include a plurality of receiving coils 170 formed in very small sizes by a CMOS process.

The plurality of receiving coils 170 may be positioned on the outer side surface of the side portion of the cage body 100 and may be positioned to correspond to the contact surface.

More specifically, the plurality of receiving coils 170 may be positioned adjacent to the contact surface formed on the side portion of the cage body 100 so as to generate electrical stimulation on the contact surface.

To this end, the plurality of receiving coils 170 may be formed to include a metal part and a wire surrounding the metal part.

Here, the plurality of receiving coils 170 may be formed in a shape in which a predetermined wire is wound around the metal part in a form of a concentric circle, a concentric ellipse, or a concentric polygon.

Additionally, the plurality of receiving coils 170 may be further connected to a matching capacitor, which may be provided as a lumped capacitor or a CMOS capacitor.

Accordingly, the system 1 may promote bone fusion using the spinal cage 10 and the power supply device 20 formed as described above.

More specifically, when axial compression occurs according to the user's movement, the system 1 may allow axial compression within a certain range through the plate springs 150*a* and 150*a*' of the spinal cage 10, thereby providing dynamic stabilization to promote bone fusion.

In addition, the system 1 may promote bone fusion by generating electrical stimulation through the receiving coils 170 of the spinal cage 10 inserted between the user's vertebrae 3 and 3' and the power supply device 20.

As described above, the detailed description of the present invention has been provided with reference to the embodiments shown in the accompanying drawings. However, the above-described embodiments are merely exemplary of the preferred embodiments of the present invention, and the present invention should not be construed as being limited thereto. The scope of the present invention should be understood according to the claims described below and equivalents thereof.

EXPLANATION OF REFERENCE MARKS

1: Electrical stimulation system
3, 3': Vertebrae
10: Spinal cage
100: Cage body
110: Bone graft filling space
130: Protrusion
150*a*, 150'*a*: Plate spring
151*a*: Upper plate spring
151*b*: Lower plate spring
153*a*, 154*a*: Crest portion
153*b*, 154*b*: Trough portion
158: Connection portion
158*a*: Center portion
170: Receiving coil
180: Front end portion
190: Rear end portion
20: Power supply device
210: Battery
220: Transmission circuit
230: Control unit
30: User terminal

The invention claimed is:

1. An electrical stimulation system comprising:

a spinal cage having a porous structure with a first side and a second side being occluded, and configured to be inserted between vertebrae of a user and deliver electrical stimulation to the user; and a power supply device configured to transmit wireless power to generate electrical stimulation to the spinal cage, and be wearable by the user, wherein the spinal cage comprises a cage body configured to surround a hollow portion defined as a bone graft filling space, wherein the cage body includes:

a first end portion having a tapered shape toward a first end;

a second end portion having a flat shape and disposed facing the first end portion;

the hollow portion defined between the first end portion and the second end portion as the bone graft filling space; and a side portion forming a side surface of the hollow portion, defined to be partially open and having a porous structure, and wherein the side portion comprises:

a plurality of contact surfaces forming a first surface and a second surface of the side portion and configured to contact the vertebrae;

a plurality of protrusions disposed on the plurality of contact surfaces at predetermined intervals in a longitudinal direction;

a plurality of plate springs disposed between the plurality of contact surfaces and configured to be deformed in response to axial pressure applied in a vertical direction; and a plurality of receiving coils positioned directly adjacent to the plurality of contact surfaces and configured to generate electrical stimulation on the plurality of contact surfaces.

2. The electrical stimulation system of claim 1, wherein the power supply device comprises:

a battery;

a transmission circuit configured to wirelessly transmit power stored in the battery to the spinal cage; and a controller configured to induce magnetic resonance in the transmission circuit using the power stored in the battery.

3. The electrical stimulation system of claim 2, wherein the controller is configured to adjust a voltage level of magnetic resonance generated in the transmission circuit based on control information input from an external source.

4. The electrical stimulation system according to claim 2, wherein the transmission circuit comprises a resonator including a loop antenna or a helical antenna having a circular or rectangular wire.

5. The electrical stimulation system of claim 1, wherein the plurality of receiving coils are positioned on an outer surface of the side portion corresponding to the plurality of contact surfaces, and includes a metal part and a wire surrounding the metal part.

6. The electrical stimulation system according to claim 5, wherein each of the plurality of receiving coils are wound around the metal part in a shape of a concentric ellipse or a concentric polygon.

7. The electrical stimulation system of claim 1, further comprising a user terminal configured to:

output a stimulation control interface screen enabling the user to control the electrical stimulation, generate control information based on a stimulation control item selected by the user through the stimulation control interface screen, and transmit the control information to the power supply device.

8. The electrical stimulation system according to claim 1, wherein the plurality of receiving coils are disposed on an outer side surface of the plurality of protrusions.

* * * * *